(12) United States Patent
Suri et al.

(10) Patent No.: US 8,808,367 B2
(45) Date of Patent: Aug. 19, 2014

(54) PROSTHETIC VALVE DELIVERY SYSTEM INCLUDING RETROGRADE/ANTEGRADE APPROACH

(75) Inventors: Rakesh Mark Suri, Rochester, MN (US); Franco Vallana, Turin (IT); Giovanni Rolando, Chivasso (IT); Giovanni Righini, Chivasso-Torino (IT); Brent Russell Phillips, Rochester, MN (US); Eric Manasse, Milan (IT)

(73) Assignees: Sorin Group Italia S.r.l., Milan (IT); Mayo Foundation for Medical Education and Research, Rochester, MN (US)

( * ) Notice: Subject to any disclaimer, the term of this patent is extended or adjusted under 35 U.S.C. 154(b) by 257 days.

(21) Appl. No.: 11/851,523

(22) Filed: Sep. 7, 2007

(65) Prior Publication Data

US 2009/0069886 A1 Mar. 12, 2009

(51) Int. Cl.
*A61F 2/24* (2006.01)

(52) U.S. Cl.
CPC .................................. *A61F 2/2436* (2013.01)
USPC ........................................................ 623/2.11

(58) Field of Classification Search
USPC ........................................................ 623/2.11
See application file for complete search history.

(56) References Cited

U.S. PATENT DOCUMENTS

| | | | |
|---|---|---|---|
| 3,671,979 A | 6/1972 | Moulopoulos | |
| 4,011,947 A | 3/1977 | Sawyer | |
| 4,056,854 A | 11/1977 | Boretos et al. | |
| 4,477,930 A | 10/1984 | Totten et al. | |
| 4,601,706 A | 7/1986 | Aillon | |
| 4,624,822 A | 11/1986 | Arru et al. | |
| 4,684,364 A | 8/1987 | Sawyer et al. | |
| 4,722,725 A | 2/1988 | Sawyer et al. | |
| 4,732,152 A | 3/1988 | Wallsten et al. | |
| 4,758,151 A | 7/1988 | Arru et al. | |
| 4,777,951 A | 10/1988 | Cribier et al. | |
| 4,784,644 A | 11/1988 | Sawyer et al. | |
| 4,994,077 A | 2/1991 | Dobben | |
| 5,057,092 A | 10/1991 | Webster, Jr. | |
| 5,084,151 A | 1/1992 | Vallana et al. | |
| 5,123,919 A | 6/1992 | Sauter et al. | |

(Continued)

FOREIGN PATENT DOCUMENTS

DE 19546692 6/1997
DE 29919625 U1 2/2000
(Continued)

OTHER PUBLICATIONS

European Search Report and Search Opinion of European Patent Application No. 06126556.7, dated Jun. 27, 2007.

(Continued)

*Primary Examiner* — Gregory Anderson
(74) *Attorney, Agent, or Firm* — Faegre Baker Daniels LLP (57) ABSTRACT

A device for implanting an expandable heart valve prosthesis at a valve annulus in a patient's heart includes an implantation device configured to extend from a first opening in the patient's body, through the patient's aorta, through a valve annulus, through an opening in a ventricle, and to exit through the patient's thoracic region. The device further includes a port having a hemostasis valve for providing access through the patient's thoracic region and into the ventricle and at least two interchangeable modules configured for delivery using the implantation device.

14 Claims, 7 Drawing Sheets

(56) References Cited

U.S. PATENT DOCUMENTS

| | | | |
|---|---|---|---|
| 5,133,845 A | 7/1992 | Vallana et al. |
| 5,181,911 A | 1/1993 | Shturman |
| 5,201,757 A | 4/1993 | Heyn et al. |
| 5,287,848 A | 2/1994 | Cubb |
| 5,304,189 A | 4/1994 | Goldberg et al. |
| 5,312,393 A | 5/1994 | Mastel |
| 5,332,402 A | 7/1994 | Teitelbaum |
| 5,370,684 A | 12/1994 | Vallana et al. |
| 5,370,685 A | 12/1994 | Stevens |
| 5,387,247 A | 2/1995 | Vallana et al. |
| 5,397,351 A | 3/1995 | Pavcnik et al. |
| 5,411,552 A | 5/1995 | Andersen et al. |
| 5,423,886 A | 6/1995 | Arru et al. |
| 5,433,723 A | 7/1995 | Lindenberg et al. |
| 5,445,646 A | 8/1995 | Euteneuer et al. |
| 5,545,214 A | 8/1996 | Stevens |
| 5,554,185 A | 9/1996 | Block et al. |
| 5,556,414 A | 9/1996 | Turi |
| 5,662,712 A | 9/1997 | Pathak et al. |
| 5,693,083 A | 12/1997 | Baker et al. |
| 5,766,151 A | 6/1998 | Valley et al. |
| 5,772,693 A | 6/1998 | Brownlee |
| 5,782,811 A | 7/1998 | Samson et al. |
| 5,824,064 A | 10/1998 | Taheri |
| 5,840,081 A | 11/1998 | Andersen et al. |
| 5,849,005 A | 12/1998 | Garrison et al. |
| 5,855,597 A | 1/1999 | Jayaraman |
| 5,855,601 A | 1/1999 | Bessler et al. |
| 5,871,489 A | 2/1999 | Ovil |
| 5,925,063 A | 7/1999 | Khosravi |
| 5,951,600 A | 9/1999 | Lemelson |
| 5,954,766 A | 9/1999 | Zadno-Azizi et al. |
| 5,957,949 A | 9/1999 | Leonhardt et al. |
| 5,980,570 A | 11/1999 | Simpson |
| 6,010,530 A | 1/2000 | Goicoechea |
| 6,010,531 A | 1/2000 | Donlon et al. |
| 6,019,756 A | 2/2000 | Mueller et al. |
| 6,019,790 A | 2/2000 | Holmberg et al. |
| 6,029,671 A | 2/2000 | Stevens et al. |
| 6,030,360 A | 2/2000 | Biggs |
| 6,090,099 A | 7/2000 | Samson et al. |
| 6,106,497 A | 8/2000 | Wang |
| 6,125,852 A * | 10/2000 | Stevens et al. ............... 128/898 |
| 6,139,572 A | 10/2000 | Campbell et al. |
| 6,168,614 B1 | 1/2001 | Andersen et al. |
| 6,174,307 B1 | 1/2001 | Daniel et al. |
| 6,251,093 B1 | 6/2001 | Valley et al. |
| 6,299,638 B1 | 10/2001 | Sauter |
| 6,309,382 B1 | 10/2001 | Garrison et al. |
| 6,346,071 B1 | 2/2002 | Mussivand |
| 6,402,780 B2 | 6/2002 | Williamson, IV et al. |
| 6,416,474 B1 | 7/2002 | Penner et al. |
| 6,425,916 B1 | 7/2002 | Garrison et al. |
| 6,454,799 B1 | 9/2002 | Schreck |
| 6,458,153 B1 | 10/2002 | Bailey et al. |
| 6,482,228 B1 | 11/2002 | Norred |
| 6,572,642 B2 | 6/2003 | Rinaldi et al. |
| 6,582,462 B1 | 6/2003 | Andersen et al. |
| 6,607,553 B1 | 8/2003 | Healy et al. |
| 6,641,558 B1 | 11/2003 | Aboul-Hosn et al. |
| 6,645,197 B2 | 11/2003 | Garrison et al. |
| 6,645,220 B1 | 11/2003 | Huter et al. |
| 6,652,578 B2 | 11/2003 | Bailey et al. |
| 6,685,739 B2 | 2/2004 | DiMatteo et al. |
| 6,726,648 B2 | 4/2004 | Kaplon et al. |
| 6,726,651 B1 * | 4/2004 | Robinson et al. ........ 604/101.01 |
| 6,726,712 B1 | 4/2004 | Raeder Devens et al. |
| 6,730,118 B2 | 5/2004 | Spenser et al. |
| 6,733,525 B2 | 5/2004 | Yang et al. |
| 6,767,362 B2 | 7/2004 | Schreck |
| 6,769,434 B2 | 8/2004 | Liddicoat et al. |
| 6,805,711 B2 | 10/2004 | Quijano et al. |
| 6,830,584 B1 | 12/2004 | Seguin |
| 6,830,585 B1 | 12/2004 | Artof et al. |
| 6,875,231 B2 | 4/2005 | Anduiza et al. |
| 6,893,460 B2 | 5/2005 | Spenser et al. |
| 6,908,481 B2 | 6/2005 | Cribier |
| 6,913,618 B2 | 7/2005 | Denardo et al. |
| 6,945,957 B2 | 9/2005 | Freyman |
| 6,964,673 B2 | 11/2005 | Tsugita et al. |
| 6,974,464 B2 | 12/2005 | Quijano et al. |
| 6,981,942 B2 * | 1/2006 | Khaw et al. ................... 600/16 |
| 6,991,646 B2 | 1/2006 | Clerc et al. |
| 7,001,423 B2 | 2/2006 | Euteneuer et al. |
| 7,018,406 B2 | 3/2006 | Seguin et al. |
| 7,018,408 B2 | 3/2006 | Bailey et al. |
| 7,041,132 B2 | 5/2006 | Quijano et al. |
| 7,044,966 B2 | 5/2006 | Svanidze et al. |
| 7,077,801 B2 | 7/2006 | Haverich |
| 7,101,396 B2 | 9/2006 | Artof et al. |
| 7,144,364 B2 | 12/2006 | Barbut et al. |
| 7,156,872 B2 | 1/2007 | Strecker |
| 7,195,641 B2 | 3/2007 | Palmaz et al. |
| 7,201,761 B2 | 4/2007 | Woolfson et al. |
| 7,329,279 B2 | 2/2008 | Salahieh et al. |
| 7,338,467 B2 | 3/2008 | Lutter |
| 7,338,520 B2 | 3/2008 | Bailey et al. |
| 7,374,571 B2 | 5/2008 | Pease et al. |
| RE40,377 E | 6/2008 | Williamson, IV et al. |
| 7,544,206 B2 | 6/2009 | Cohn |
| 7,556,646 B2 | 7/2009 | Yang et al. |
| 7,591,843 B1 | 9/2009 | Escano et al. |
| 7,618,432 B2 | 11/2009 | Pedersen et al. |
| 7,635,386 B1 * | 12/2009 | Gammie ..................... 623/2.11 |
| 7,708,775 B2 | 5/2010 | Rowe et al. |
| 7,896,915 B2 * | 3/2011 | Guyenot et al. ............ 623/2.14 |
| 7,993,392 B2 | 8/2011 | Rihhini et al. |
| 8,057,539 B2 | 11/2011 | Ghione et al. |
| 8,070,799 B2 | 12/2011 | Righini et al. |
| 8,114,154 B2 | 2/2012 | Righini et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0039450 A1 | 11/2001 | Pavcnik et al. |
| 2001/0044591 A1 | 11/2001 | Stevens et al. |
| 2002/0029075 A1 | 3/2002 | Leonhardt |
| 2002/0042651 A1 | 4/2002 | Liddicoat et al. |
| 2002/0045846 A1 | 4/2002 | Kaplon et al. |
| 2002/0058995 A1 | 5/2002 | Stevens |
| 2002/0099431 A1 | 7/2002 | Armstrong et al. |
| 2002/0107531 A1 | 8/2002 | Schreck et al. |
| 2002/0117264 A1 | 8/2002 | Rinaldi et al. |
| 2002/0123802 A1 | 9/2002 | Snyders |
| 2002/0138138 A1 | 9/2002 | Yang |
| 2002/0151970 A1 | 10/2002 | Garrison et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0033000 A1 | 2/2003 | DiCaprio et al. |
| 2003/0036795 A1 | 2/2003 | Andersen et al. |
| 2003/0055495 A1 | 3/2003 | Pease et al. |
| 2003/0109924 A1 | 6/2003 | Cribier |
| 2003/0130729 A1 | 7/2003 | Paniagua et al. |
| 2003/0153974 A1 | 8/2003 | Spenser et al. |
| 2003/0163194 A1 | 8/2003 | Quijano et al. |
| 2003/0191521 A1 | 10/2003 | Denardo et al. |
| 2003/0191528 A1 | 10/2003 | Quijano et al. |
| 2004/0034411 A1 | 2/2004 | Quijano et al. |
| 2004/0039371 A1 | 2/2004 | Tockman et al. |
| 2004/0039436 A1 | 2/2004 | Spenser et al. |
| 2004/0039442 A1 | 2/2004 | St. Goar et al. |
| 2004/0049266 A1 | 3/2004 | Anduiza et al. |
| 2004/0055606 A1 | 3/2004 | Hendricksen et al. |
| 2004/0078072 A1 | 4/2004 | Tu et al. |
| 2004/0093060 A1 | 5/2004 | Seguin et al. |
| 2004/0093063 A1 | 5/2004 | Wright et al. |
| 2004/0106976 A1 | 6/2004 | Bailey et al. |
| 2004/0127848 A1 | 7/2004 | Freyman |
| 2004/0147993 A1 | 7/2004 | Westlund et al. |
| 2004/0186563 A1 | 9/2004 | Lobbi |
| 2004/0215333 A1 | 10/2004 | Duran et al. |
| 2004/0236170 A1 | 11/2004 | Kim |
| 2004/0249413 A1 | 12/2004 | Allen et al. |

(56) References Cited

U.S. PATENT DOCUMENTS

| | | |
|---|---|---|
| 2005/0075584 A1 | 4/2005 | Cali |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075726 A1 | 4/2005 | Svanidze et al. |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0080476 A1 | 4/2005 | Gunderson et al. |
| 2005/0096993 A1 | 5/2005 | Pradhan et al. |
| 2005/0104957 A1 | 5/2005 | Okamoto et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Salahieh et al. |
| 2005/0137693 A1 | 6/2005 | Haug et al. |
| 2005/0137694 A1 | 6/2005 | Salahieh et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143809 A1 | 6/2005 | Salahieh et al. |
| 2005/0165480 A1 | 7/2005 | Jordan et al. |
| 2005/0197695 A1 | 9/2005 | Stacchino et al. |
| 2005/0240200 A1 | 10/2005 | Bergheim |
| 2005/0251251 A1 | 11/2005 | Cribier |
| 2005/0267493 A1* | 12/2005 | Schreck et al. ............... 606/139 |
| 2005/0278010 A1 | 12/2005 | Richardson |
| 2006/0004436 A1 | 1/2006 | Amarant et al. |
| 2006/0004439 A1 | 1/2006 | Spenser et al. |
| 2006/0020333 A1 | 1/2006 | Lashinski et al. |
| 2006/0020334 A1 | 1/2006 | Lashinski et al. |
| 2006/0025844 A1 | 2/2006 | Majercak et al. |
| 2006/0030922 A1 | 2/2006 | Dolan |
| 2006/0063199 A1 | 3/2006 | Elgebaly et al. |
| 2006/0064054 A1 | 3/2006 | Sakakine et al. |
| 2006/0074271 A1 | 4/2006 | Cotter |
| 2006/0074484 A1 | 4/2006 | Huber |
| 2006/0085060 A1 | 4/2006 | Campbell |
| 2006/0095025 A1 | 5/2006 | Levine et al. |
| 2006/0100639 A1 | 5/2006 | Levin et al. |
| 2006/0135962 A1 | 6/2006 | Kick et al. |
| 2006/0142838 A1 | 6/2006 | Molaei et al. |
| 2006/0142848 A1 | 6/2006 | Gabbay |
| 2006/0178740 A1 | 8/2006 | Stacchino et al. |
| 2006/0195134 A1 | 8/2006 | Crittenden |
| 2006/0195184 A1 | 8/2006 | Lane et al. |
| 2006/0229659 A1 | 10/2006 | Gifford et al. |
| 2006/0241656 A1 | 10/2006 | Starksen |
| 2006/0271081 A1 | 11/2006 | Realyvasquez |
| 2006/0276775 A1 | 12/2006 | Rosenberg et al. |
| 2007/0010850 A1 | 1/2007 | Balgobin et al. |
| 2007/0027534 A1 | 2/2007 | Bergheim et al. |
| 2007/0032850 A1 | 2/2007 | Ruiz et al. |
| 2007/0055357 A1 | 3/2007 | Pokorney et al. |
| 2007/0088431 A1 | 4/2007 | Bourang et al. |
| 2007/0100302 A1 | 5/2007 | Dicarlo et al. |
| 2007/0100356 A1 | 5/2007 | Lucatero et al. |
| 2007/0100440 A1 | 5/2007 | Figulla et al. |
| 2007/0112355 A1 | 5/2007 | Salahieh et al. |
| 2007/0112422 A1 | 5/2007 | Dehdashtian |
| 2007/0118207 A1 | 5/2007 | Amplatz et al. |
| 2007/0118209 A1 | 5/2007 | Strecker |
| 2007/0156225 A1 | 7/2007 | George et al. |
| 2007/0162100 A1 | 7/2007 | Gabbay |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0162113 A1 | 7/2007 | Sharkawy et al. |
| 2007/0173861 A1 | 7/2007 | Strommer et al. |
| 2007/0203503 A1 | 8/2007 | Salahieh et al. |
| 2007/0203561 A1 | 8/2007 | Forster et al. |
| 2007/0203575 A1 | 8/2007 | Forster et al. |
| 2007/0219630 A1 | 9/2007 | Chu |
| 2007/0250097 A1 | 10/2007 | Weitzner et al. |
| 2007/0265702 A1 | 11/2007 | Lattouf |
| 2008/0021546 A1 | 1/2008 | Patz et al. |
| 2008/0065011 A1 | 3/2008 | Marchand et al. |
| 2008/0082165 A1 | 4/2008 | Wilson et al. |
| 2008/0097595 A1 | 4/2008 | Gabbay |
| 2008/0140189 A1 | 6/2008 | Nguyen et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0147188 A1 | 6/2008 | Steinberg |
| 2008/0183097 A1 | 7/2008 | Leyde et al. |
| 2008/0208216 A1 | 8/2008 | Cerier |
| 2008/0262507 A1 | 10/2008 | Righini et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0069890 A1 | 3/2009 | Suri et al. |
| 2009/0105794 A1 | 4/2009 | Ziarno et al. |
| 2009/0118580 A1 | 5/2009 | Sun et al. |
| 2009/0157174 A1 | 6/2009 | Yoganathan et al. |
| 2009/0164004 A1 | 6/2009 | Cohn |
| 2009/0164006 A1 | 6/2009 | Seguin et al. |
| 2009/0171363 A1 | 7/2009 | Chocron |
| 2009/0171456 A1 | 7/2009 | Kveen et al. |
| 2009/0177275 A1 | 7/2009 | Case |
| 2009/0228093 A1 | 9/2009 | Taylor et al. |
| 2009/0234443 A1 | 9/2009 | Ottma et al. |
| 2009/0240326 A1 | 9/2009 | Wilson et al. |
| 2009/0254165 A1 | 10/2009 | Tabor et al. |
| 2009/0281609 A1 | 11/2009 | Benichou et al. |
| 2009/0281619 A1 | 11/2009 | Le et al. |
| 2010/0191326 A1 | 7/2010 | Alkhatib |
| 2010/0292782 A1 | 11/2010 | Giannetti et al. |
| 2010/0292783 A1 | 11/2010 | Giannetti et al. |
| 2010/0292784 A1 | 11/2010 | Giannetti et al. |
| 2012/0053684 A1 | 3/2012 | Righini et al. |
| 2013/0123915 A1 | 5/2013 | Giannetti et al. |

FOREIGN PATENT DOCUMENTS

| | | |
|---|---|---|
| DE | 19857887 | 7/2000 |
| DE | 19857887 A1 | 5/2005 |
| EP | 0133420 | 2/1988 |
| EP | 0155245 B1 | 5/1990 |
| EP | 0592410 | 10/1995 |
| EP | 0512359 | 12/1996 |
| EP | 0515324 B1 | 12/1996 |
| EP | 0850607 | 7/1998 |
| EP | 1057460 | 12/2000 |
| EP | 1059271 A1 | 12/2000 |
| EP | 1088529 | 4/2001 |
| EP | 1356763 A2 | 10/2003 |
| EP | 1356793 | 10/2003 |
| EP | 0852481 B1 | 2/2004 |
| EP | 1440671 A2 | 7/2004 |
| EP | 1088529 B1 | 6/2005 |
| EP | 0955895 B1 | 8/2005 |
| EP | 1488735 B1 | 6/2007 |
| EP | 1212989 B1 | 1/2008 |
| EP | 1653884 B1 | 6/2008 |
| EP | 1935377 A1 | 6/2008 |
| EP | 1955643 A1 | 8/2008 |
| EP | 1986579 B1 | 11/2008 |
| EP | 1570809 B1 | 1/2009 |
| EP | 2033581 A1 | 3/2009 |
| EP | 2033597 A1 | 3/2009 |
| FR | 2828091 | 2/2003 |

(56) References Cited

FOREIGN PATENT DOCUMENTS

| | | |
|---|---|---|
| WO | WO9511055 A1 | 4/1995 |
| WO | 9724989 | 7/1997 |
| WO | 9817202 | 4/1998 |
| WO | 9829057 | 7/1998 |
| WO | WO9853761 A1 | 12/1998 |
| WO | WO 99/04728 A1 | 2/1999 |
| WO | 9956665 | 11/1999 |
| WO | WO 00/18303 A1 | 4/2000 |
| WO | 0041652 | 7/2000 |
| WO | WO 00/41525 A2 | 7/2000 |
| WO | WO 01/021244 A1 | 3/2001 |
| WO | 0162189 | 8/2001 |
| WO | 0164137 | 9/2001 |
| WO | 0176510 | 10/2001 |
| WO | 0241789 | 5/2002 |
| WO | 0247575 | 6/2002 |
| WO | 02076348 | 10/2002 |
| WO | 03003943 | 1/2003 |
| WO | 03094797 | 11/2003 |
| WO | WO2004019825 A1 | 3/2004 |
| WO | WO2004028399 A2 | 4/2004 |
| WO | 2004089253 | 10/2004 |
| WO | WO 2005/046525 A1 | 5/2005 |
| WO | WO 2005/065200 A2 | 7/2005 |
| WO | WO 2005/096993 A1 | 10/2005 |
| WO | 2005/104957 | 11/2005 |
| WO | 2005104957 | 11/2005 |
| WO | 2006054107 | 5/2006 |
| WO | 2006/063199 | 6/2006 |
| WO | 2006063199 | 6/2006 |
| WO | WO 2006/086135 A2 | 8/2006 |
| WO | 2006116558 | 11/2006 |
| WO | WO 2006/135551 A2 | 12/2006 |
| WO | WO 2006/138173 A2 | 12/2006 |
| WO | WO2007021708 A1 | 2/2007 |
| WO | WO 2007/071436 A2 | 6/2007 |
| WO | WO 2007/076463 A2 | 7/2007 |
| WO | WO 2008/097589 A1 | 8/2008 |
| WO | WO 2008/125153 A1 | 10/2008 |

OTHER PUBLICATIONS

Huber et al., "Direct-Access Valve Replacement: A Novel Approach for Off-Pump Valve Implantation Using Valved Stents," Journal of the American College of Cardiology, 46(2): 366-370, Jul. 19, 2002.
U.S. Appl. No. 11/612,968, filed Dec. 19, 2006.
U.S. Appl. No. 11/612,972, filed Dec. 19, 2006.
U.S. Appl. No. 11/612,974, filed Dec. 19, 2006.
U.S. Appl. No. 11/612,980, filed Dec. 19, 2006.
U.S. Appl. No. 11/851,523, filed Sep. 7, 2007.
U.S. Appl. No. 11/851,528, filed Sep. 7, 2007.
Huber et al., "Direct-Access Valve Replacement: A Novel Approach for Off-Pump Valve Implantation Using Valved Stents", Journal of the American College of Cardiology, pp. 366-370, vol. 46, No. 2, Jul. 19, 2005, ISSN: 0735-1097/05, published on-line Jul. 5, 2005.
Righini et al., U.S. Appl. No. 11/612,980, filed Dec. 19, 2006, "Instrument and Method for in Situ Deployment of Cardiac Valve".
Righini et al., U.S. Appl. No. 11/851,528, filed Sep. 7, 2007, "Fluid-Filled Delivery System for in Situ Deployment of Cardiac Valve Prostheses".
European Search Report Issued in EP Application No. 09160183, dated Oct. 2, 2009, 6 pages.
European Search Report Issued in EP Application No. 09160186, dated Oct. 6, 2009, 5 pages.
European Search Report Issued in EP Application No. 07115951, dated Sep. 24, 2009, 8 pages.
Extended European Search Report issued in EP Application 06126552, dated Jun. 6, 2007, 7 pages.
Extended European Search Report issued in EP Application 09158822, dated Sep. 9, 2009, 5 pages.
Ho, Paul C., "Percutaneous aortic valve replacement: A novel design of the delivery and deployment system", Minimally Invasive Therapy, 2008; 17:3; 190-194.
European Search Report and Search Opinion of European Patent Application No. 07115960.2, dated Jan. 24, 2008.
European Search Report Issued in EP 09160184 dated Oct. 22, 2009.
European Search Report issued in EP Application 08163752, dated Dec. 29, 2008.
Extended European Search Report issued in EP Application 06126556, dated Jul. 6, 2007, 13 pages.
Extended European Search Report issued in EP Application 09158822, dated Sep. 29, 2009, 5 pages.
Huber et al., "Direct-Access Valve Replacement: A Novel Approach for Off-Pump Valve Implantation Using Valved Stents", Journal for the American College of Cardiology, pp. 366-370, vol. 46, No. 2, Jul. 19, 2005, ISSN: 0735-1097/05, published on-line Jul. 5, 2005.
Partial European Search Report issued in EP App No. 06126556, mailed Apr. 16, 2007, 6 pages.
European Search Report issued in EP Application No. 08159301, mailed Dec. 30, 2008, 6 pages.
Partial European Search Report issued in EP Application No. 10155332, dated Jun. 9, 2011, 7 pages.
European Search Report issued in EP 11182402, mailed Nov. 16, 2011, 5 pages.

\* cited by examiner

PROSTHETIC VALVE DELIVERY SYSTEM INCLUDING RETROGRADE/ANTEGRADE APPROACH

TECHNICAL FIELD

The present invention relates generally to methods and systems for cardiovascular surgery. More particularly, the invention relates to methods and systems for the repair, removal and/or replacement of heart valves.

BACKGROUND

Minimally-invasive percutaneous valve replacement procedures have emerged as an alternative to open-chest surgery, using intravascular catheterization (e.g., from a femoral artery access point) or a minimally-invasive surgical technique. Because the minimally-invasive approach requires only a small incision, it allows for a faster recovery for the patient with less pain and bodily trauma. This, in turn, reduces the medical costs and the overall disruption to the life of the patient.

An inherent difficulty in the minimally-invasive percutaneous approach is the limited space that is available within the vasculature. Unlike open heart surgery, minimally-invasive heart surgery offers a surgical field that is only as large as the diameter of a blood vessel. Consequently, the introduction of tools and prosthetic devices is challenging. The device must be dimensioned and configured to permit it to be introduced into the vasculature, maneuvered therethrough, and positioned at a desired location. Moreover, lesions located in the vasculature may be a contraindication for certain types of delivery systems using femoral access.

Thus, there is a need in the art for methods and devices for performing heart valve repair and replacement, as well as other procedures within the heart and great vessels that provide greater ease of access to native heart valves.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
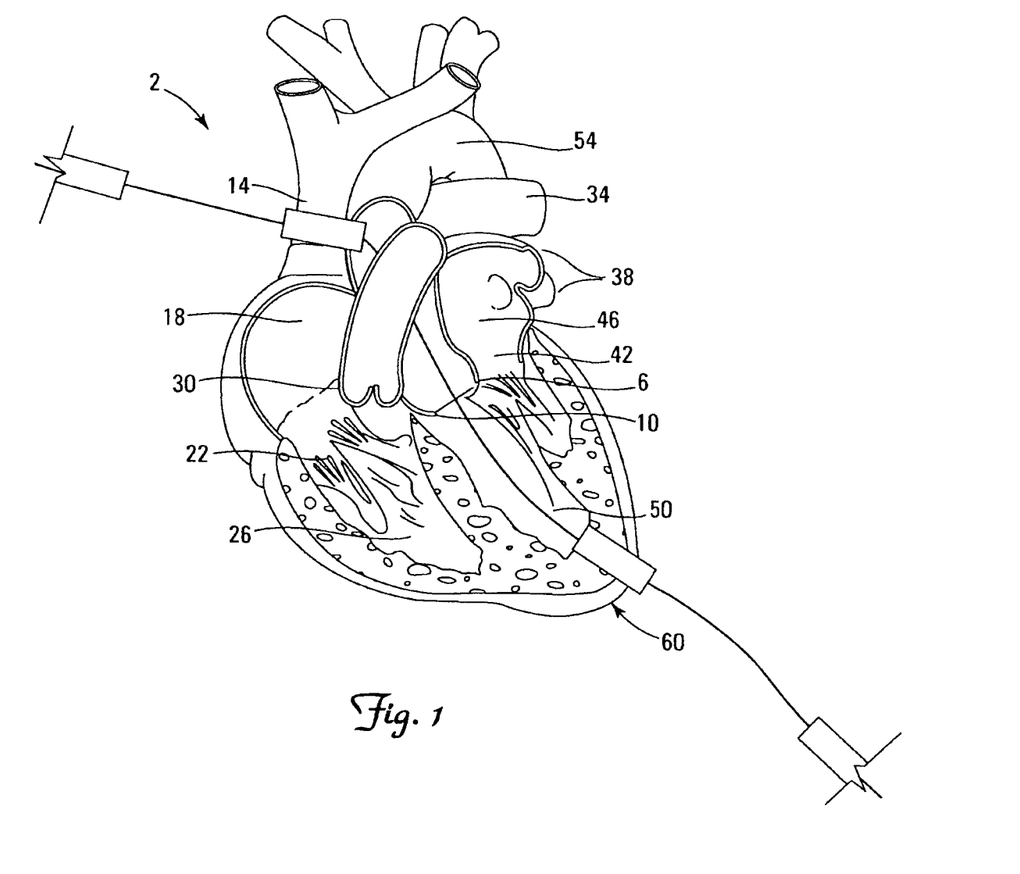
FIG. 1 is a cross-sectional view of a human heart including a prosthetic heart valve.

FIG. 1 is a cross-sectional view of a human heart 2 with an expandable prosthetic heart valve 6 implanted within or adjacent an aortic valve annulus 10. Blood flows from the superior and inferior vena cavas 14 into a right atrium 18 of the heart 2 and then flows through a tricuspid valve 22 into a right ventricle 26. A pulmonary valve 30 facilitates blood flow from the right ventricle 26 to the pulmonary arteries 34. The blood is then oxygenated by the lungs and returned back to the heart via pulmonary veins 38. A mitral valve 42 then facilitates blood flow from a left atrium 46 to a left ventricle 50. Blood then flows from the left ventricle 50, through the aortic valve annulus 10, to the aorta 54. The aorta 54 then delivers the blood to the coronary arteries and the peripheral vascular system.

Using techniques well known to those of skill in the art, access to the heart 2, according to some embodiments, is established percutaneously through the aorta, femoral, radial or brachial arteries using a retrograde approach to reach a target site within the heart 6 (e.g. the aorta 54 or aortic valve annulus 10). Likewise, according to some embodiments, access to the aortic valve annulus is accomplished using a retrograde, minimally-invasive surgical technique to provide access to the aortic valve annulus 10 through an opening in the aortic arch.

Alternatively, according to various embodiments, access to the heart 2 and the aortic valve annulus 10 is established through the apical area 60 (e.g., apex) of the heart. In these embodiments, a percutaneous access port may be established through a patient's chest wall and into the left ventricle at or near the apex 60. According to some embodiments, access to the left ventricle 50 through the apex 60 is established using one of the methods and devices generally shown and described in U.S. Pat. No. 6,010,531, entitled "Less-invasive Devices and Methods for Cardiac Valve Surgery", which is incorporated herein by reference.

The apex 60 of the heart 2 is generally the blunt rounded inferior extremity of the heart 2 formed by the left and right ventricles, 26 and 50. In normal healthy humans, the apex 60 generally lies behind the fifth left intercostal space from the mid-sternal line. Access to the valve annulus 10 through the apex 60 can be established using a larger diameter access port than is possible using percutaneous access methods. Thus, apical access to the heart 2 permits greater flexibility with respect to the types of devices and surgical methods that may be performed in the heart and great vessels.

FIGS. 2-6 show schematic views of exemplary embodiments of a valve access system 70 for delivering a replacement heart valve to a target site in a patient's heart 2. The valve access system 70 of the present invention allows for an antegrade as well as a retrograde approach to a target site within the heart 2. Exemplary target sites include native heart valves (e.g. pulmonary, mitral, aortic, and tricuspid) needing repair and/or replacement. While FIGS. 2-6 show the valve access system 70 traveling through the aortic arch, in alternative embodiments, the system 70 could exit the vasculature through the aorta and patient's body through a slit or opening in the wall of the aortic vessel.

Figure 2:
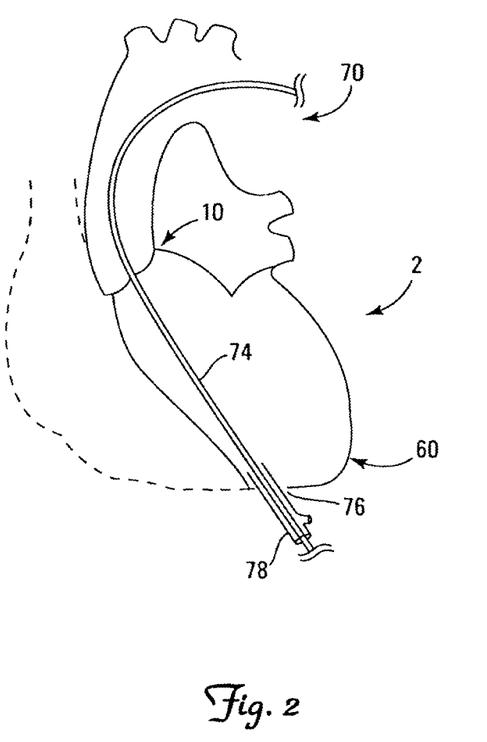
FIG. 2 is a schematic view of the left side of the heart including an implantation device according to an embodiment of the present invention.

According to the embodiment of FIG. 2, the valve access system 70 includes an implantation device 74 and is configured to deliver a prosthetic heart valve to a target site within a patient's heart 2. The implantation device 74 is configured to serve as a rail or track for providing access to the target site from a location outside the patient's body. According to one embodiment of the present invention, the implantation device 74 is a thin, flexible guidewire or a somewhat thicker wire, such as a stylet. According to an alternative embodiment of the present invention, the implantation device is a guide catheter. The guide catheter is adapted to provide passage to a variety of devices compatible with the valve access system of the present invention. According to one embodiment, the implantation device is reversibly lockable.

The implantation device 74 is of sufficient size and length to pass through a first opening in a patient's body (e.g., an aorta or a femoral artery access point), through a patient's aorta 54, and to exit through an access port 76 established in a patient's left ventricle 50 at or near the apex 60. The implantation device 74 then extends through a transthoracic port 78, which provides access through the patient's thoracoabdominal (e.g., intercostal) region and into the left ventricle 50 at or near the apex 60. The transthoracic port according to various exemplary embodiments is one of an introducer, trocar, or cannula, as is generally known in the art. According to one exemplary embodiment of the present invention, the port 78 includes one or more hemostasis valves or seals. The hemostasis valve or seal is adapted to provide a blood tight seal against any blood loss or leakage during the procedure, and can be used at the apex, at the aorta, or in both locations. The port 78 is configured to allow passage of the implantation device, catheter, or any tools or devices to be delivered to the target site using the implantation device, while at the same time providing a blood tight seal against blood loss or leakage.

According to one exemplary technique for introducing the access system 70, a physician establishes an access port into the patient's aorta or femoral artery using any of a variety of well-known techniques. The physician then establishes a second access point in the patient's intercostal region using the port 78. Using known imaging and guidance techniques, the physician then advances the implantation device 74 through the patient's aorta or arterial system to the aortic valve annulus 10. The physician then advances the implantation device 74 across the aortic valve annulus 10, through the left ventricle 50, and out of the heart through the port 78. At this point, the physician has established a continuous pathway allowing both retrograde (i.e., through the aorta or aortic arch) and antegrade (i.e., through the apex 60) access to the aortic valve annulus 10.

According to another exemplary embodiment, the implantation device 74 includes two portions. The physician introduces a first portion through the aorta or femoral artery to the aortic valve annulus 10 and introduces a second portion through the apex 60. According to various embodiments, the physician then couples the two portions together at or near the valve annulus 10 or the aortic root. In these embodiments, the implantation device 74 includes any of a variety of known structures for coupling the free ends to one another, so as to form a continuous rail or track. According to other embodiments, the physician employs any of a numerous variety of techniques known in the art to introduce the implantation device 74. According to various embodiments, the physician employs one or more of the following techniques to implant the device 74: optionally ballooning the native valve in one variant of the invention, or removing the native valve (e.g., by cutting the valve out of the annulus), optionally using an umbrella capture feature to catch any debris that may result from the cut, and implanting the device 74.

Once introduced, the implantation device 74 establishes a pathway between a first opening and second opening in a patient's body. The implantation device is left in place within the heart 2 to provide a tether or "rail" over which other tools or devices may be delivered. Additional tools and devices may be delivered along the rail using either a retrograde (i.e., via the aorta) or an antegrade (i.e., via the apex and left ventricle) approach. The implantation device 74 allows for one or more than one device to be delivered to the target site at the same time or substantially at the same time. This feature allows flexibility in delivery options and may increase the speed in the successive steps in the valve replacement procedure.

By way of further example, one tool or set of tools can be delivered through the access port from the aorta while a second tool or set of tools can be delivered through the access point in the left ventricle, along a single track spanning both points of access or along separate tracks, one for each access point. An aortic valve (which can be stenotic in many patients) cutter or remover is delivered through the access point in the aorta by a first physician or technician. The native stenotic valve (e.g., aortic valve) is excised, stored in a chamber of the cutter, and then the cutter assembly is removed through the aortic access point. A delivery system for an expandable valve prosthesis can be guided through the ventricular access port and be positioned in the ventricle ready for immediate insertion into position once the cutting operation has been completed. The delivery system can be optionally operated by a second physician or technician and be ready and waiting for deployment. It is appreciated that the speed with which both the cutting and the valve prosthesis deployment operations is greatly increased and the procedure time is greatly reduced using a combination antegrade and retrograde delivery approach. In this way the hemodynamic blood flow for the patient is maintained at an acceptable level while the patient is off-pump or partially off-pump. Similarly, it is appreciated that a variety of tools or modules (or portions thereof) can be guided either antegrade or retrograde along the guidewire.

In various exemplary embodiments of the invention, the cutter or native valve leaflet remover is sized and dimensioned to be delivered through the apex of the heart, while the delivery system including a heart valve prosthesis is sized and dimensioned for delivery through an access point on the aorta. In yet another variant of the invention, an access point can be established at any suitable point in the aortic tree.

By way of further example, a top portion of the cutter can be guided into cutting position along the guidewire along from the aortic access point, while a bottom portion of a cutter can be guided along the guidewire through the access point in the ventricle. The two portions meet at the native valve and perform the cutting and removal operation and then are each removed through the same access areas where they entered the patient.

By way of further example, other modules that can travel along the guidewire can include pumps for assisting in maintaining the patient's hemodynamic flow. The pumps can be positioned in various locations along the guidewire as needed. Other modules (e.g., a cutter or prosthesis delivery module) can then be guided over the pumps to perform their required operations.

As described, the valve access system 70 allows for delivery of a variety of devices to or near the aortic valve annulus 10. The system 70 may be used for example to introduce any of a variety of prosthetic heart valves, including, for example, stented and stentless tissue valves. The system 70 may also be used to introduce an imaging system to view all or a portion of a procedure. Imaging systems are well-known in the art and include, for example, transesophageal echo, transthoracic echo, intravascular ultrasound imaging (IVUS), and/or a radiopaque dye or contrast fluid. The imaging system may also include an optical viewing device, such as a fiber-optic camera.

The valve access system 70 allows for delivery of a variety of additional tools or devices, including, for example, the following: leaflet excision tools, leaflet capture devices, imaging devices, prosthetic heart valves, prosthetic valve delivery systems, blood-pump devices, inflation catheters and balloons, debris capture collapsible and expandable umbrellas, stenotic tissue debridement tools, markers located on the guidewire to assist in location of the guidewire at the appropriate location, centering balloons to center the guidewire in the desired orientation, and the like. In yet a further variant, an anti-embolization module is also added. According to various embodiments, the leaflet excision module includes a rigid portion having an actuator exerting sufficient force to cut through a calcified leaflet.

According to another embodiment of the present invention, the valve access system includes one or more interchangeable modules that are configured to be delivered along the implantation device 74 to the valve annulus 10. The implantation device 74 permits one or more modules to be in use at a given time, in series or in parallel. Depending upon the size of the module, an antegrade, retrograde, or combination antegrade and retrograde delivery approach may be chosen. As the apex 60 is not limited by the size constraints which are presented by percutaneous surgical methods, larger modules or devices may be delivered through the port 78. Smaller modules may continue to be delivered through the femoral artery approach or directly through a port or incision in the aorta. Ultimately either approach may be chosen at the discretion of one of skill in the art performing the procedure.

In yet another embodiment of the invention, all modules are de-aired, filled with a fluid (e.g., saline), or filled with an appropriate gas (e.g., carbon dioxide or nitrogen) prior to use. This process eliminates the risk of an embolism occurring through the introduction of any of the modules described below directly into the beating heart of the subject. According to various embodiments, the modules are de-aired using one of the techniques described in co-pending, commonly assigned U.S. patent application Ser. No. 11/851,528, filed on even date herewith, entitled "Fluid-Filled Delivery System for in Situ Deployment of Cardiac Valve Prostheses," which is hereby incorporated by reference in its entirety.

Figure 3:
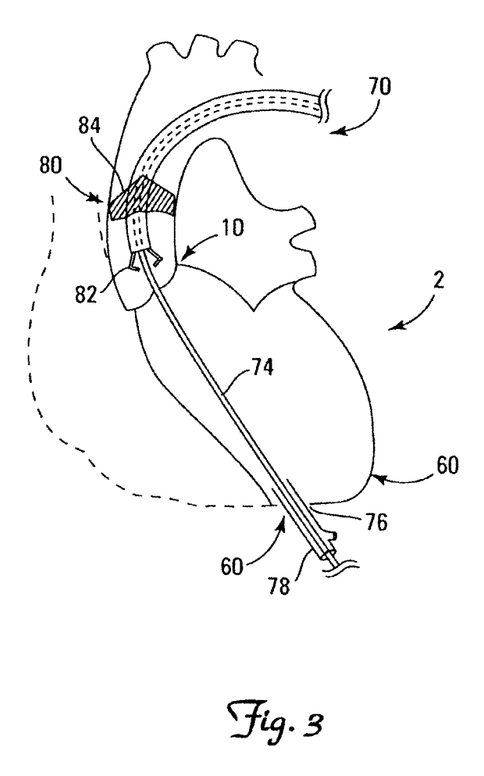
FIG. 3 is a schematic view of the left side of the heart including an implantation device and one interchangeable module according to an embodiment of the present invention.

According to the embodiment of the present invention shown in FIG. 3, the valve access system 70 includes a leaflet removal (i.e., excision) module 80, which may include a leaflet cutting tool 82. The leaflet removal module 80 includes a rigid portion having an actuator exerting sufficient force to cut through a calcified leaflet. The actuator can be hydraulically or mechanically actuated to provide sufficient force to cut through stenotic native valve tissue. In various embodiments, the actuator is spring actuated. In yet another variant, the actuator is gas actuated. Exemplary leaflet removal or cutting tools are shown and described in U.S. Pat. No. 5,304, 189, U.S. Pat. No. 5,370,685, and U.S. Publication 2006/ 0271081, each of which are incorporated herein by reference.

According to yet a further embodiment of the present invention, as is also shown in FIG. 3, the valve access system 70 also includes a leaflet capture device 84. The leaflet capture device 84 captures the removed portion or portions of the leaflet upon excision and traps any debris from the removal or decalcification of the leaflets. The capture device 84 entraps and contains the debris or excised portions. The capture device permits removal of the debris from the patient's heart 2.

Figure 4A:
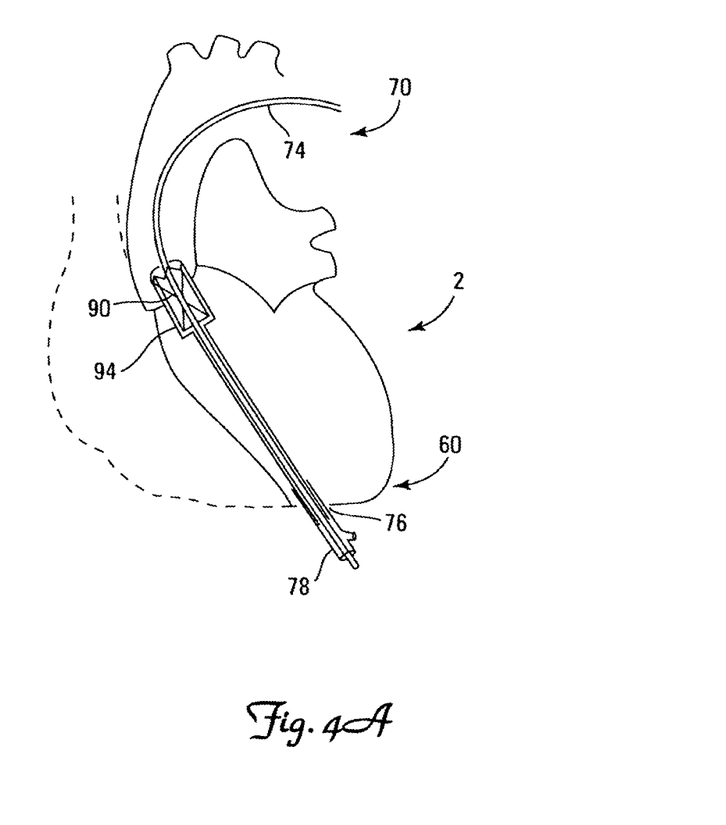
FIGS. 4A and 4B are schematic views of the of the left side of the heart including an implantation device and another interchangeable module according to another embodiment of the present invention.
Figure 4B:
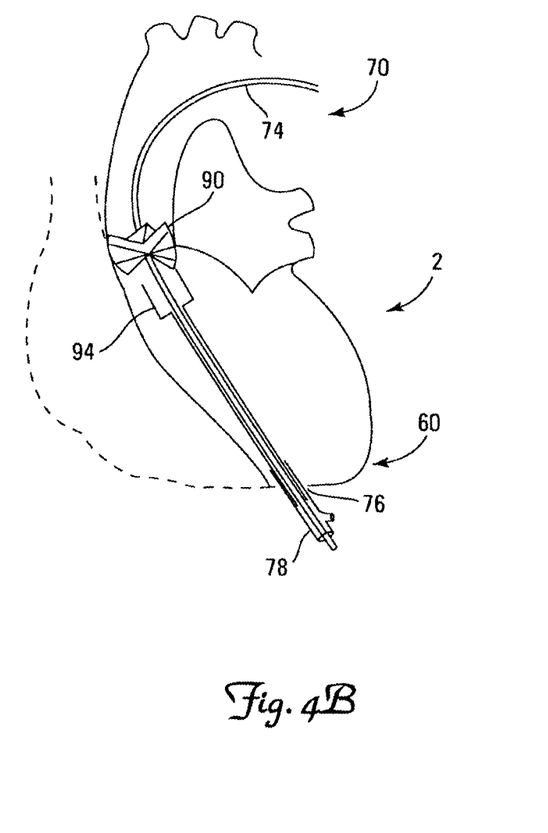

FIGS. 4A and 4B show another embodiment of the valve access system 70 of the present invention. As shown in FIG. 4A, the system 70 includes an expandable prosthetic heart valve 90 retained in a collapsed configuration within a delivery sheath 94. As described previously, the heart valve 90 can be crimped onto the delivery system 70 under water, such that the sheath is fluid filled to prevent embolism. Exemplary expandable prosthetic heart valves are shown and described in U.S. Publication 2006/0178740 and U.S. Publication 2005/ 0197695, both of which are incorporated herein by reference. An exemplary delivery system for an expandable prosthetic valve is shown and described in commonly-assigned, co-pending U.S. application Ser. No. 11/612,980, entitled "Instrument and Method for In-Situ Deployment of Cardiac Valve Prosthesis", which is incorporated herein by reference. As shown in FIG. 4A, the prosthetic valve 90 has been delivered over the implantation device 74 to a target site within or near the aortic valve annulus 10 via an access port established at or near the apex 60. As shown, in FIG. 4B, the delivery sheath 94 can be retracted allowing the expandable prosthetic heart valve 90 to transition from a collapsed configuration to an expanded configuration, after which the implantation device 74 can be removed. According to other embodiments, the delivery sheath 94 could be introduced in a retrograde manner through the aorta or optionally through the aortic arch.

Figure 5:
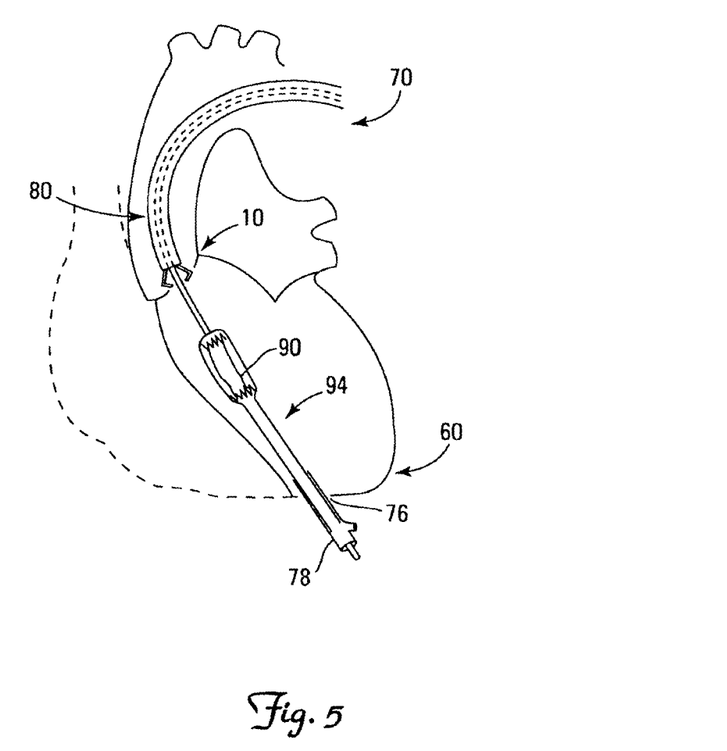
FIG. 5 is a schematic view of the left side of the heart including an implantation device and two interchangeable modules according to yet another embodiment of the present invention.

FIG. 5 shows an embodiment of the valve access system 70 of the present invention, which includes two interchangeable modules. As shown in FIG. 5, the valve access system 70 includes an implantation device 74 and a first module being delivered using an antegrade approach and a second module being delivered using a retrograde approach. According to one embodiment of the present invention, the modules have different functionalities. For example, in various embodiments, the first module is a leaflet cutter 80 and the second module is an expandable prosthetic valve 90 contained within a delivery sheath 94. After the leaflets have been excised from the valve annulus, the expandable prosthetic valve 90 can be quickly delivered and released to expand within the valve annulus. This configuration can help reduce the time that a patient's heart is beating, without a functioning valve in place, by allowing a physician to deliver both a valve removal device and a valve delivery device at or near the valve annulus 10, before actually removing the valve leaflets. The configuration is thus helpful for off-pump, beating heart prosthetic valve replacement.

Figure 6:
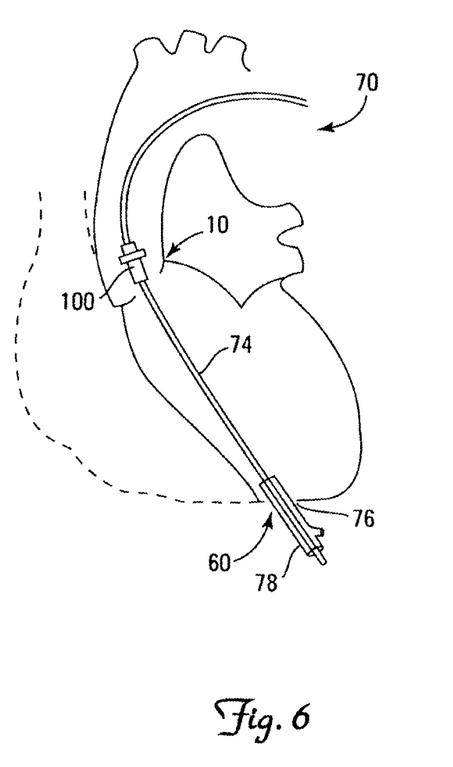
FIG. 6 is a schematic view of the left side of the heart including an implantation device and yet another interchangeable module according to yet another embodiment of the present invention.

According to yet a further embodiment of the present invention, as shown in FIG. 6, the valve access system 70 includes a blood-pumping device 100. For example, the blood pumping device is a left ventricular assist device (LVAD) known to those of skill in the art. Exemplary LVADs are shown and described in U.S. Pat. No. 7,144,364, which is incorporated herein by reference. The LVAD can be delivered using either an antegrade or a retrograde approach along the pathway established by the implantation device 74. The LVAD is then delivered to a target site within the left ventricle or the aorta.

In yet another variant of the invention, two distinct mechanically unconnected tracks are used upon which two mechanically unconnected modules are utilized. In this variant, a first module is configured to be delivered from a first opening in a patient's aortic tree and through the patient's aorta. One or more of the modules described herein may be used. A second module is configured to be delivered through an opening in a ventricle. Again, one or more modules described herein may be used. As with the other embodiments described herein, the fact that two simultaneous or nearly simultaneous access points are used on the patient allows for speed of native valve removal and implantation of a new prosthesis.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An access system for implanting an expandable heart valve prosthesis at an aortic valve annulus in a patient's heart, the access system comprising:
   a transthoracic access port, including one or more hemostasis valves or seals, that are configured to be used at or near an opening in a left ventricle, and
   a second port, including one or more hemostasis valves or seals, that are configured to be used at or near an aortic wall opening;
   a guidewire having a sufficient size and length to extend through a first opening in the patient's body, through the opening in the patient's aortic wall, through the patient's aorta, through the valve annulus in the patient's heart, through the opening in the left ventricle at or near an apex of the patient's heart, and through an opening in the patient's thoracoabdominal region, the guidewire being structurally continuous and having a sufficient length to extend continuously between the transthoracic access port and the second port;
   a first module configured for retrograde delivery along the guidewire through the first opening and through the aortic wall opening toward the valve annulus; and
   a second module, not mechanically coupled to the first module, the second module configured for antegrade delivery along the guidewire through the thoracoabdominal region opening and the opening in the ventricle toward the valve annulus;
   wherein the first or second module is selected from a group consisting of a ballooning module, a leaflet cutting or removal module, an annulus sizing module, an expandable valve prosthesis module, a pump module, and a debris catching module.

2. The access system of claim 1, wherein the leaflet cutting or removal module comprises a rigid portion having an actuator exerting sufficient force to cut through a calcified leaflet.

3. The access system of claim 1, wherein the guidewire is a stylet.

4. The access system of claim 1, wherein the modules can be delivered to the target location within the heart using either of an antegrade approach or a retrograde approach.

5. The access system of claim 1, wherein the guidewire is bendable and steerable.

6. The access system of claim 5 in which the guidewire is reversibly lockable.

7. The access system of claim 1, wherein the transthoracic access port is selected from a group comprising: an introducer, a trocar and a cannula.

8. The access system of claim 1, wherein at least one of the first or second module includes an imaging system to view all or a portion of a procedure.

9. The access system of claim 8, wherein the imaging system includes a device selected from the group comprising: a transesophogeal echo, transthoracic echo, intravascular ultrasound imaging, and/or a radiopaque dye or contrast fluid.

10. The access system of claim 9, wherein the imaging system also includes an optical viewing device.

11. The access system of claim 1, wherein the first module comprises a leaflet cutter and the second module comprises an expandable prosthetic heart valve contained within a delivery sheath.

12. The access system of claim 1, wherein at least one of the first and second modules includes at least one pump for assisting in maintaining the patient's hemodynamic flow, with the at least one pump being positionable at various locations along the guidewire.

13. An access system for implanting an expandable heart valve prosthesis at an aortic valve annulus in a patient's heart, the access system comprising:
   a guidewire having a sufficient size and length to extend through a first opening in the patient's body, through an opening or slit in the patient's aortic wall, through the patient's aorta, through the valve annulus in the patient's heart, through an opening in a left ventricle at or near the apex of the patient's heart, and through an opening in the patient's thoracoabdominal region, the guidewire being structurally continuous;
   a first module configured for retrograde delivery along the guidewire through the first opening and through the aortic wall opening toward the valve annulus; and
   a second module, not mechanically coupled to the first module, the second module configured for antegrade delivery along the guidewire through the thoracoabdominal region opening and the opening in the ventricle toward the valve annulus;
   and
   a transthoracic access port, including one or more hemostasis valves or seals, that are configured to be used at or near the ventricle opening, and
   a second port, including one or more hemostasis valves or seals, that are configured to be used at or near the aortic wall opening;
   wherein the first or second module is selected from a group consisting of a ballooning module, a leaflet cutting or removal module, an annulus sizing module, an expandable valve prosthesis module, a pump module, and a debris catching module, wherein the first module includes a top portion of the leaflet cutting or removal module and the second module includes a bottom portion of the leaflet cutting or removal module, wherein the top and bottom portions can be guided to and meet at the valve annulus to perform a cutting and removal operation.

14. An access system for implanting an expandable heart valve prosthesis at an aortic valve annulus in a patient's heart, the access system comprising:
   a guidewire having a sufficient size and length to extend through a first opening in the patient's thoracoabdominal region, through an opening in a left ventricle at or near the apex of the heart, through the aortic valve annulus, through an opening or slit in the patient's aortic wall, and through an opening in the patient's body at or near the aorta, the guidewire being structurally continuous;
   a first module configured for retrograde delivery along the guidewire through the first opening and the aortic wall opening toward the valve annulus;
   a second module, not mechanically coupled to the first module, the second module configured for antegrade delivery along the guidewire through the thoracoabdominal region opening and the opening in the ventricle toward the valve annulus, wherein the first or second module is selected from a group consisting of a ballooning module, a leaflet cutting or removal module, an annulus sizing module, an expandable valve prosthesis module, a pump module and a debris catching module; and a transthoracic access port, including one or more hemostasis valves or seals, that are configured to be used at or near the ventricular opening, and a second port, including one or more hemostasis valves or seals, that are configured to be used at or near the aortic wall opening.

* * * * *